(12) United States Patent
Fageon et al.

(10) Patent No.: US 11,534,386 B2
(45) Date of Patent: Dec. 27, 2022

(54) EMULSION COMPRISING AN ANIONIC ACRYLIC COPOLYMER AND A LIPOPHILIC POLYMER

(71) Applicant: L'OREAL, Paris (FR)

(72) Inventors: Laure Fageon, Chevilly la Rue (FR); Carole Guiramand, Chevilly la Rue (FR); Karl Boutelet, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/761,357

(22) PCT Filed: Nov. 15, 2018

(86) PCT No.: PCT/EP2018/081470
§ 371 (c)(1),
(2) Date: May 4, 2020

(87) PCT Pub. No.: WO2019/096955
PCT Pub. Date: May 23, 2019

(65) Prior Publication Data
US 2021/0169770 A1    Jun. 10, 2021

(30) Foreign Application Priority Data
Nov. 15, 2017  (FR) ...................................... 1760738

(51) Int. Cl.
| | | |
|---|---|---|
| *A61K 8/81* | (2006.01) | |
| *A61K 8/06* | (2006.01) | |
| *A61Q 1/14* | (2006.01) | |
| *A61Q 17/04* | (2006.01) | |
| *A61Q 19/00* | (2006.01) | |
| *A61Q 19/08* | (2006.01) | |
| *A61Q 19/10* | (2006.01) | |

(52) U.S. Cl.
CPC ............ *A61K 8/8152* (2013.01); *A61K 8/062* (2013.01); *A61Q 1/14* (2013.01); *A61Q 17/04* (2013.01); *A61Q 19/00* (2013.01); *A61Q 19/08* (2013.01); *A61Q 19/10* (2013.01); *A61K 2800/594* (2013.01)

(58) Field of Classification Search
None
See application file for complete search history.

(56) References Cited

U.S. PATENT DOCUMENTS

| | | |
|---|---|---|
| 4,128,635 A | 12/1978 | Hase et al. |
| 2004/0005279 A1 | 1/2004 | Lorant et al. |
| 2007/0264204 A1 | 11/2007 | Noor et al. |
| 2020/0281829 A1* | 9/2020 | Guiramand .......... A61K 8/4973 |
| 2020/0297612 A1* | 9/2020 | Dou ......................... A61K 8/06 |
| 2020/0345621 A1* | 11/2020 | Lorant ..................... A61K 8/31 |
| 2021/0177719 A1* | 6/2021 | Lorant ..................... A61K 8/06 |

FOREIGN PATENT DOCUMENTS

| | | |
|---|---|---|
| EP | 3 235 839 A1 | 10/2017 |
| JP | 2015131767 A * | 7/2015 |

OTHER PUBLICATIONS

JPO English abstract for JP 2015-131767 A (Year: 2015).*
Machine-assisted English translation for JP 2015-131767 A (Year: 2015).*

* cited by examiner

*Primary Examiner* — Sin J Lee
(74) *Attorney, Agent, or Firm* — Polsinelli PC

(57) ABSTRACT

Emulsion comprising an anionic acrylic copolymer and a lipophilic polymer A subject of the present invention is a composition in the form of an emulsion, preferably in the form of an oil-in-water emulsion, comprising at least one hydrophilic gelling polymer chosen from anionic acrylic copolymers and at least one lipophilic polymer comprising at least hydroxyethyl acrylate units and acrylate units bearing a lipophilic group, wherein the weight ratio of the sum of all the hydroxyethyl acrylate units to the sum of all the acrylate units bearing a lipophilic group ranges from 1:30 to 1:1 and wherein the lipophilic polymer has a number-average molecular weight Mn ranging from 2000 to 9000 g/mol. The composition in accordance with the invention makes it possible to obtain emulsions which are homogeneous (the emulsion is macroscopically smooth and has no grains, after storage in a pot for 24 hours at ambient temperature (25° C.)), which have a variable viscosity (very fluid to very thick), which are stable over time, and which have good sensory properties, in particular which are non-tacky, non-shiny and non-greasy on the skin.

26 Claims, No Drawings

EMULSION COMPRISING AN ANIONIC ACRYLIC COPOLYMER AND A LIPOPHILIC POLYMER

CROSS REFERENCE TO RELATED APPLICATIONS

This application is a National Phase filing under 35 U.S.C. § 371 of PCT/EP2018/081470 filed on 15 Nov. 2018; which application in turn claims priority to Application No. 1760738 filed in France on 15 Nov. 2017. The entire contents of each application are hereby incorporated by reference.

The present application relates to a composition in the form of an emulsion comprising at least one hydrophilic gelling polymer chosen from anionic acrylic copolymers and at least one suitably selected lipophilic polymer, and to the use of said composition in the cosmetics and dermatology fields, in particular for caring for, treating keratin materials, and in particular for caring for, protecting and/or making up bodily or facial skin, or for hair care. Care products in an overall manner provide benefits to the skin, whether they are visual and/or perceived, and this is true in the various axes of application of the cosmetics industry, from care to makeup and including anti-sun products. To do this, active molecules or ingredients, such as UV-screening agents, are introduced into the compositions.

However, the stability of the emulsions is fragile and is easily degraded when these materials are added. To stabilize the compositions, it has been proposed to use high contents of emulsifiers in order to increase the robustness of the architecture, which results in compromising the sensoriality and sometimes the innocuousness and the comfort on the skin of these products.

Furthermore, the formulation of these materials can cause negative effects such as:

sensoriality problems, such as tacky and/or greasy effects on the skin; and formula stability problems, causing in particular a phase separation of the emulsions.

There therefore remains the need to produce stable, homogeneous compositions which have improved cosmetic properties and which are in particular less tacky, less shiny and less greasy during and after application to the skin and which have good robustness, that is to say that they retain these properties after addition of active molecules or of ingredients such as UV-screening agents.

Surprisingly, the applicant has discovered that the combination of at least one aqueous gelling polymer chosen from anionic acrylic copolymers and of at least one suitably selected lipophilic polymer makes it possible to meet this need, and in particular to obtain robust emulsions which are homogeneous, stable over time and with respect to temperature, which have good sensory properties, in particular which are non-tacky, non-shiny and non-greasy on the skin, this being in a wide viscosity range (very fluid to very thick).

Thus, a subject of the present invention is a composition in the form of an emulsion comprising at least one hydrophilic gelling polymer chosen from anionic acrylic copolymers and at least one lipophilic polymer comprising monomeric units of formulae (A) and (B):

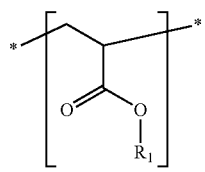

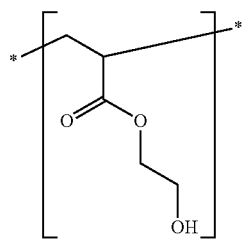

in which:

$R_1$, independently of one another, are chosen from alkyl or alkylene radicals;

with at least 60% by weight of the $R_1$ groups being behenyl radicals, the percentage by weight relating to the sum of all the $R_1$ groups present in the polymer;

the weight ratio of the sum of all the hydroxyethyl acrylate units to the sum of all the acrylate units bearing the $R_1$ group ranges from 1:30 to 1:1; and the sum of the total of units of A and B is at least 95% by weight of the total weight of the polymer.

The composition according to the invention is intended for topical application and thus comprises a physiologically acceptable medium. The term "physiologically acceptable medium" here is intended to mean a medium that is compatible with keratin materials.

In the context of the present invention, the term "keratin material" especially is intended to mean the skin, the scalp, keratin fibres such as the eyelashes, the eyebrows, head hair, bodily hair, the nails, and mucous membranes such as the lips, and more particularly the skin (body, face, area around the eyes, eyelids).

The composition in accordance with the invention makes it possible to obtain emulsions which are homogeneous (the emulsion is macroscopically smooth and has no grains, after storage in a pot for 24 hours at ambient temperature (25° C.)), which have a variable viscosity (very fluid to very thick), which are stable over time, and which have good sensory properties, in particular which are non-tacky, non-shiny and non-greasy on the skin.

For the purposes of the present invention, the term "stable" is intended to mean stable at ambient temperature (AT), 4° C. and 45° C. and at atmospheric pressure for 15 days, preferably for 1 month, and even better still for 2 months. The composition is considered to be stable when its macroscopic and microscopic appearances, its viscosity and its pH show little change, or even no change at all.

A subject of the invention is also a cosmetic treatment process for caring for and/or making up keratin materials, which consists in applying to the keratin materials a composition as defined above.

A subject of the invention is also the use of said composition in cosmetics or dermatology, and in particular for caring for, protecting and/or making up bodily or facial skin, or for haircare.

In the following text, the expression "at least one" is equivalent to "one or more" and, unless otherwise indicated, the limits of a range of values are included in that range.

Hydrophilic (Aqueous) Gelling Polymers

The composition according to the invention comprises at least one hydrophilic gelling polymer chosen from anionic acrylic copolymers.

The term "hydrophilic gelling polymer" is intended to mean a polymer that is capable of thickening an aqueous medium. Preferably, the thickening polymer has, at 1% in water or a 50/50 water/alcohol mixture by weight at 25° C., a viscosity of greater than 100 centipoise at a shear rate of 1 s$^{-1}$. These viscosities can be measured using in particular viscometers or rheometers having cone-plate geometry.

For the purposes of the present invention, the term "acrylic copolymer" is intended to mean a polymer resulting from the copolymerization of at least two chemically different monomers, at least one of which is chosen from unsaturated carboxylic acids, preferably acrylic acid or methacrylic acid.

According to a particular embodiment of the invention, the anionic acrylic copolymer(s) are chosen from:

anionic copolymers derived from at least one unsaturated carboxylic acid and from at least one ester of an unsaturated carboxylic acid and of a monoalcohol comprising from 1 to 6 carbon atoms and preferably from 1 to 4 carbon atoms; and anionic associative acrylic copolymers.

For the purposes of the present invention, the term "associative polymer" is intended to mean an amphiphilic polymer that is capable, in an aqueous medium, of reversibly combining with itself or with other molecules. It generally comprises, in its chemical structure, at least one hydrophilic region or group and at least one hydrophobic region or group.

The term "hydrophobic group" is intended to mean a group or a polymer bearing a saturated or unsaturated and linear or branched hydrocarbon-based chain. When it denotes a hydrocarbon-based group, the hydrophobic group comprises at least 8 carbon atoms, preferably from 10 to 30 carbon atoms, in particular from 12 to 24 carbon atoms and preferentially from 16 to 22 carbon atoms. Preferentially, the hydrocarbon-based hydrophobic group originates from a monofunctional compound. By way of example, the hydrophobic group may be derived from a fatty alcohol, such as stearyl alcohol, dodecyl alcohol or decyl alcohol, or else from a polyalkylenated fatty alcohol, such as steareth-100. It may also denote a hydrocarbon-based polymer, for instance polybutadiene. In the context of the invention, the anionic copolymer(s) derived from at least one unsaturated carboxylic acid and from at least one ester of an unsaturated carboxylic acid and of a monoalcohol comprising from 1 to 6 carbon atoms and preferably from 1 to 4 carbon atoms are different from the anionic associative acrylic copolymer(s).

The anionic copolymer(s) derived from at least one unsaturated carboxylic acid and from at least one ester of an unsaturated carboxylic acid and of a monoalcohol comprising from 1 to 6 carbon atoms and preferably from 1 to 4 carbon atoms are copolymers comprising, among their monomers, one or more unsaturated carboxylic acids, which are more particularly α,β-monoethylenically unsaturated, and one or more esters of an unsaturated carboxylic acid, which are more particularly α,β-monoethylenically unsaturated, and of a monoalcohol comprising from 1 to 6 carbon atoms and preferably from 1 to 4 carbon atoms.

More particularly, the unsaturated carboxylic acid, which is in particular α,β-monoethylenically unsaturated, is a monomer corresponding to formula (I) below:

$$H_2C=\underset{R^1}{\overset{}{C}}-\underset{O}{\overset{\|}{C}}-OH \qquad (I)$$

in which $R^1$ denotes H or $CH_3$ or $C_2H_5$, which corresponds to acrylic acid, methacrylic acid or ethacrylic acid units.

Preferably, the other monomeric ester of an unsaturated carboxylic acid and of a monoalcohol comprising from 1 to 6 carbon atoms and preferably from 1 to 4 carbon atoms is a monomer of formula (II) below:

$$H_2C=\underset{R^1}{\overset{}{C}}-\underset{O}{\overset{\|}{C}}-OR^2 \qquad (II)$$

in which $R^1$ denotes H or $CH_3$ or $C_2H_5$ (i.e. acrylate, methacrylate or ethacrylate units) and preferably H (acrylate units) or $CH_3$ (methacrylate units), and $R^2$ denotes an alkyl group comprising from 1 to 6 carbon atoms and preferably from 1 to 4 carbon atoms.

As esters of an unsaturated carboxylic acid and of a fatty monoalcohol comprising from 1 to 6 carbon atoms according to formula (II), mention may be made more particularly of methyl acrylate, ethyl acrylate, propyl acrylate and butyl acrylate, and the corresponding methacrylates, methyl methacrylate, ethyl methacrylate, propyl methacrylate and butyl methacrylate.

According to one embodiment, these anionic copolymers may be crosslinked, for example, with a crosslinking agent, which is a well-known copolymerizable polyethylenic unsaturated monomer, for instance diallyl phthalate, allyl (meth)acrylate, divinylbenzene, (poly)ethylene glycol dimethacrylate or methylenebisacrylamide.

Among anionic copolymers of this type, use will more particularly be made of the polymers constituted of the following monomers:

i) of an unsaturated carboxylic acid, which is in particular α,β-monoethylenically unsaturated, corresponding to formula (I) below:

$$H_2C=\underset{R^1}{\overset{}{C}}-\underset{O}{\overset{\|}{C}}-OH \qquad (I)$$

in which $R^1$ denotes H or $CH_3$ or $C_2H_5$, which corresponds to acrylic acid, methacrylic acid or ethacrylic acid units;

(ii) of an ester of an unsaturated carboxylic acid and of a monoalcohol comprising from 1 to 6 carbon atoms and preferably from 1 to 4 carbon atoms, of formula (II) below:

$$H_2C=\underset{R^1}{\overset{}{C}}-\underset{O}{\overset{\|}{C}}-OR^2 \qquad (II)$$

in which $R^1$ denotes H or $CH_3$ or $C_2H_5$ (i.e. acrylate, methacrylate or ethacrylate units) and preferably H (acrylate units) or $CH_3$ (methacrylate units), and $R^2$ denotes an alkyl group comprising from 1 to 6 carbon atoms and preferably from 1 to 4 carbon atoms, (iii) and optionally a crosslinking agent, which is a well-known copolymerizable polyethylenic unsaturated monomer, such as diallyl phthalate, allyl (meth)acrylate, divinylbenzene, (poly)ethylene glycol dimethacrylate or methylenebisacrylamide.

Examples of anionic copolymers as defined above are the crosslinked copolymer of acrylic acid and of ethyl acrylate sold under the trade name Aculyn 33 by the company Röhm & Haas, which is in aqueous dispersion containing 28% by weight of active material, the methacrylic acid/ethyl acrylate crosslinked copolymer in the form of an aqueous dispersion at 30% by weight sold under the name Carbopol Aqua SF-1 Polymer by the company Lubrizol, and the copolymer of (meth)acrylic acid and of a $C_1$-$C_4$ alkyl (meth)acrylate sold under the name Synthalen W400 by the company 3V Sigma, at 30% by weight of active material in water.

Preferably, these anionic copolymers are chosen from crosslinked copolymers of (meth)acrylic acid and of a $C_1$-$C_4$ alkyl (meth)acrylate, and better still from crosslinked copolymers of (meth)acrylic acid and of ethyl (meth)acrylate.

Among the anionic associative acrylic copolymers that may be used in the context of the invention, mention may be made of:

(1) copolymers derived from the polymerization of:
(i) (meth)acrylic acid,
(ii) a monomer of formula (III) below:

(III)

in which R' denotes H or $CH_3$, B denotes the ethyleneoxy group (—$CH_2$—$CH_2$—O—), n is zero or denotes an integer ranging from 1 to 100 (especially from 5 to 15) and R denotes a hydrocarbon-based group chosen from alkyl, arylalkyl, aryl, alkylaryl and cycloalkyl groups comprising from 8 to 30 carbon atoms, preferably from 10 to 24 carbon atoms and even more particularly from 16 to 20 carbon atoms.

A monomer of formula (III) that is more particularly preferred is a monomer in which R' denotes H, n is equal to 10 and R denotes a stearyl (C18) group.

Such anionic associative polymers are described in patent EP-0 216 479.

Among these anionic associative polymers, the ones that are particularly preferred are polymers formed from 20% to 60% by weight of (meth)acrylic acid, from 5% to 60% by weight of $C_1$-$C_4$ alkyl (meth)acrylate, from 2% to 50% by weight of monomer of formula (III), and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, preference is given most particularly to terpolymers of methacrylic acid, ethyl acrylate and polyoxyethylenated stearyl alcohol allyl ether containing 10 mol of ethylene oxide (INCI name: Steareth-10 allyl ether/acrylates copolymer), especially in 40/50/10 respective weight proportions, such as the product sold under the name Salcare SC 80 by the company Ciba;

(2) associative polymers comprising at least one hydrophilic unit of unsaturated ethylenic carboxylic acid type and at least one hydrophobic unit of ($C_{10}$-$C_{30}$)alkyl ester of unsaturated carboxylic acid type.

Preferably, these polymers are chosen from copolymers of (i) a monomer of formula (IV) below:

(IV)

in which $R^1$ denotes H or $CH_3$ or $C_2H_5$, and of (ii) monomer of the following formula (V) (monomer of ($C_{10}$-$C_{30}$)alkyl ester of unsaturated carboxylic acid type):

(V)

in which $R^1$ denotes H or $CH_3$ or $C_2H_5$ and preferably H or $CH_3$, $R^3$ denotes a $C_{10}$-$C_{30}$ and preferably $C_{12}$-$C_{22}$ alkyl group.

In this polymer, the monomer (IV) constitutes the hydrophilic unit and the monomer (V) constitutes the hydrophobic unit.

($C_{10}$-$C_{30}$)alkyl esters of unsaturated carboxylic acids comprise, for example, lauryl (meth)acrylate, stearyl (meth)acrylate, decyl (meth)acrylate, isodecyl (meth)acrylate and dodecyl (meth)acrylate.

Anionic polymers of this type are described and prepared, for example, according to U.S. Pat. Nos. 3,915,921 and 4,509,949.

Among the anionic associative polymers of this type that will be used more particularly are polymers formed from a monomer mixture comprising:

(i) acrylic acid, (ii) an ester of formula (V) described above in which $R^1$ denotes H or $CH_3$ and $R^3$ denotes an alkyl group containing from 12 to 22 carbon atoms, (iii) and optionally a crosslinking agent, which is a well-known copolymerizable polyethylenic unsaturated monomer, such as diallyl phthalate, allyl (meth)acrylate, divinylbenzene, (poly)ethylene glycol dimethacrylate or methylenebisacrylamide.

Among the anionic associative polymers of this type, use will be made more particularly of:

those constituted of 95% to 60% by weight of acrylic acid, 4% to 40% by weight of a $C_{10}$-$C_{30}$ alkyl acrylate and 0 to 6% by weight of a crosslinking polymerizable monomer, or alternatively those constituted of 98% to 96% by weight of acrylic acid, 1% to 4% by weight of a $C_{10}$-$C_{30}$ alkyl acrylate and 0.1% to 0.6% by weight of a crosslinking polymerizable monomer, such as those described previously.

Among the abovementioned polymers, the ones that are most particularly preferred are the products sold by the company Lubrizol under the trade names Pemulen TR1, Pemulen TR2, Carbopol 1382, Carbopol ETD 2020, Carbopol Ultrez 20 and Carbopol Ultrez 21 (INCI name: Acrylates/010-30 alkyl acrylate crosspolymer), and even more preferentially Pemulen TR1 and Carbopol 1382;

(3) acrylic terpolymers comprising:

(a) from 19.5% to 70% by weight of an α,β-monoethylenically unsaturated carboxylic acid containing from 3 to 5 carbon atoms, (b) from 20% to 80% by weight of $C_1$-$C_4$ alkyl (meth) acrylates, (c) from 0.5% to 60% by weight of a non-ionic urethane macromonomer of formula (VI) below:

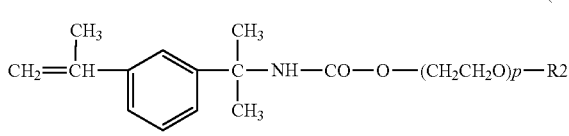

(VI)

in which p ranges from 6 to 150 and R2 is chosen from linear alkyl radicals comprising from 18 to 26 and preferably from 20 to 24 carbon atoms. Preferably, the radical R2 is a behenyl radical.

Such terpolymers are described especially in patent application EP-A-0 173 109.

The α,β-monoethylenically unsaturated carboxylic acid (a) may be chosen from acrylic acid, methacrylic acid and crotonic acid. It is preferably (meth)acrylic acid. Preferentially, the monomer (a) is methacrylic acid.

The terpolymer contains a monomer (b) chosen from $C_1$-$C_4$ alkyl (meth)acrylates such as methyl (meth)acrylate, ethyl (meth)acrylate or butyl (meth)acrylate. The monomer (b) is preferably chosen from methyl acrylate and ethyl acrylate.

Such terpolymers are generally in the form of an aqueous dispersion.

Use is preferentially made of a terpolymer of methacrylic acid/methyl acrylate/condensate of dimethyl meta-isopropenyl benzyl isocyanate and of polyoxyethylenated (40 OE) behenyl alcohol (INCI name: Polyacrylate-3), such as the product sold in the form of an aqueous dispersion at 25% by weight, under the name Viscophobe DB 1000 by the company The Dow Chemical Company;

(4) copolymers of an α,β-monoethylenically unsaturated carboxylic acid and of an ester of an α,β-monoethylenically unsaturated carboxylic acid and of a polyoxyethylenated C12-C30 fatty alcohol, especially with 10 to 50 ethylene oxide units, and of an ester of an α,β-monoethylenically unsaturated carboxylic acid and of a $C_1$-$C_4$ alcohol.

Examples of such copolymers that may be mentioned include:

polymers of acrylic acid, of methyl acrylate and of 20 OE polyoxyethylenated stearyl methacrylate crosslinked with pentaerythrityl allyl ether or trimethylolpropane allyl ether (INCI name: Acrylates/steareth-20 methacrylate crosspolymer) sold under the name Aculyn 88 Polymer by the company The Dow Chemical Company, crosslinked polymers of acrylic acid, of methyl acrylate and of 25 OE polyoxyethylenated behenyl methacrylate (INCI name: Acrylates/beheneth-25 methacrylate copolymer), such as the product sold under the name Novethix L-10 Polymer by the company Lubrizol Advanced Materials, Inc., polymers of acrylic acid, of methyl acrylate and of 25 OE polyoxyethylenated C12-C24 alkyl methacrylate (INCI name: Acrylates/palmeth-25 acrylate copolymer), such as the product sold under the name Synthalen W2000 L by the company 3V Group, polymers of methacrylic acid, of ethyl methacrylate, of polyethylene glycol C16-C22 alkyl ether methacrylate containing 25 ethylene glycol units, of the ether of 2-(6,6-dimethylbicyclo[3.1.1]hept-2-en-2-yl)ethyl methacrylate and of polypropylene glycol containing 5 propylene glycol units and of polyethylene glycol containing 25 ethylene glycol units (INCI name: Polyacrylate-33), such as the product sold under the name Rheomer® 33 by the company Rhodia Novecare.

the polyoxyethylenated (20 OE) terpolymer of acrylic acid/ethyl acrylate/stearyl methacrylate (INCI name: Acrylates/steareth-20 methacrylate copolymer) sold especially under the name Aculyn 22 by the company The Dow Chemical Company, the polyoxyethylenated (25 OE) terpolymer of acrylic acid/ethyl acrylate/behenyl methacrylate (INCI name: Acrylates/beheneth-25 methacrylate copolymer) sold especially under the name Aculyn 28 Polymer by the company The Dow Chemical Company;

(5) copolymers of (meth)acrylic acid, of crosslinked $C_1$-$C_4$ alkyl (meth)acrylate, of polyethylene glycol $C_{10}$-$C_{30}$ alkyl ether methacrylate containing 25 mol of ethylene oxide and of polyethylene glycol allyl ether containing 20 ethylene oxide units/polypropylene glycol containing 5 propylene oxide units, such as the product sold under the name Fixate® Plus Polymer by the company Lubrizol (INCI name: Polyacrylate-14).

According to one particular embodiment, the associative polymers as described above have a weight-average molecular weight of less than 500 000 and even more preferentially of less than 100 000, preferably ranging from 5000 to 80 000, which may be measured via the methods known to those skilled in the art.

The hydrophilic gelling polymer(s) chosen from anionic acrylic copolymers can be present in the composition according to the invention in a content of active material ranging from 0.1% to 2% by weight, relative to the total weight of the composition, preferably ranging from 0.2% to 1.5% by weight, preferentially ranging from 0.3% 1% by weight, and even more preferentially from 0.5% to 1% by weight.

Lipophilic Polymers

The composition in accordance with the invention comprises at least one lipophilic polymer comprising monomeric units of formulae (A) and (B):

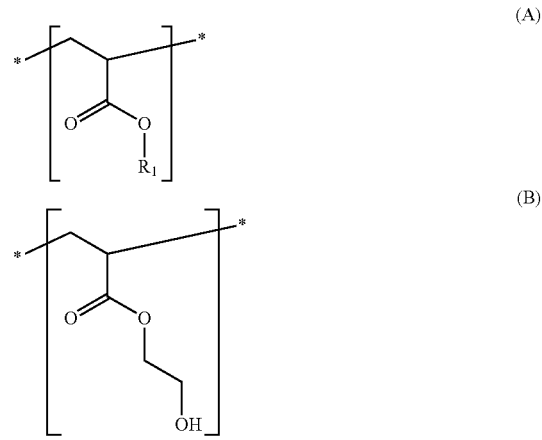

in which:

$R_1$, independently of one another, are chosen from alkyl or alkylene radicals;

with at least 60% by weight of the $R_1$ groups being behenyl radicals, the percentage by weight relating to the sum of all the $R_1$ groups present in the polymer;

the weight ratio of the sum of all the hydroxyethyl acrylate units to the sum of all the acrylate units bearing the $R_1$ group ranges from 1:30 to 1:1; and the sum of the total of units A and B is at least 95% by weight of the total weight of the polymer.

Preferably, $R_1$ is constituted of alkyl radicals, preferably of $C_{16}$-$C_{22}$ alkyl radicals, and more preferentially of behenyl ($C_{22}$) radicals.

Preferably, at least 70% by weight of the $R_1$ groups are behenyl radicals, preferentially at least 80% by weight, and more preferentially at least 90% by weight.

According to one preferred embodiment, all the $R_1$ groups are behenyl radicals.

Preferably, said weight ratio ranges from 1:15 to 1:1, preferentially ranges from 1:10 to 1:4.

Advantageously, the polymeric units present in the polymer are constituted of the units (A) and (B) previously described.

The polymer has a number-average molecular weight Mn ranging from 2000 to 9000 g/mol, preferably ranging from 5000 to 9000 g/mol. The number-average molecular weight can be measured with the gel permeation chromatography method, for example according to the method described in the example hereinafter.

Preferably, the polymer has a melting point ranging from 60° C. to 69° C., and preferentially ranging from 63° C. to 67° C. The melting point is measured by differential scanning calorimetry (DSC), for example according to the method described in the example hereinafter.

The polymer used according to the invention can be prepared by polymerization of the monomer of formula $CH_2$=CH—COO—$R_1$, $R_1$ having the meaning previously described, and of 2-hydroxyethyl acrylate.

The polymerization can be carried out according to known methods, such as solution polymerization or emulsion polymerization.

The polymerization is, for example, described in document US 2007/0264204.

The lipophilic polymer(s) used in the context of the invention and as previously described can be present in the composition in an amount of active material ranging from 0.1% to 10% by weight, preferably from 0.1% to 3% by weight, relative to the total weight of the composition.

The composition according to the invention is in the form of an emulsion and can be prepared according to the usual methods.

According to one particular embodiment, the composition according to the invention is in the form of an oil-in-water emulsion (direct emulsion) comprising a continuous aqueous phase and an oily phase dispersed in said aqueous phase.

According to another particular embodiment, the composition according to the invention is in the form of a water-in-oil emulsion (inverse emulsion) comprising a continuous oily phase and an aqueous phase dispersed in said oily phase.

Preferably, the composition according to the invention is in the form of an oil-in-water emulsion.

According to one particular embodiment, the composition in accordance with the present invention has a viscosity that can range from 20 mPa·s (ultra-fluid formula) to 100 mPa·s (creamy formula), or even up to 10 Pa·s (thick formulae), the measurements being carried out at 25° C. with a Rheomat 180 with spindle 1, 2, 3 or 4 (depending on the viscosity range) at 200 $s^{-1}$.

Fatty Phase

The composition according to the invention comprises at least one fatty phase.

The proportion of the fatty phase can range for example from 1% to 80% by weight, preferably from 5% to 40% by weight, relative to the total weight of the composition.

For the purpose of the invention, the fatty phase includes any fatty substance that is liquid at ambient temperature and atmospheric pressure, generally oils, or that is solid at ambient temperature and atmospheric pressure, like pasty compounds or waxes.

For the purposes of the present invention, the term "pasty compound" is intended to mean a compound that is water-immiscible and that undergoes a reversible solid/liquid change of state and that comprises in the solid state an anisotropic crystal organization, and comprises, at a temperature of 23° C., a liquid fraction and a solid fraction.

For the purposes of the present invention, the term "wax" is intended to mean a lipophilic compound, which is solid at ambient temperature (25° C.), with a reversible solid/liquid change of state, which has a melting point of greater than or equal to 30° C. that may be up to 120° C.

The melting point of the wax may be measured using a differential scanning calorimeter (D.S.C.), for example the calorimeter sold under the name DSC 30 by the company Mettler. Preferably, the measuring protocol is as follows:

A sample of 5 mg of wax placed in a crucible is subjected to a first temperature rise passing from −20° C. to 100° C., at a heating rate of 10° C./minute, it is then cooled from 100° C. to −20° C. at a cooling rate of 10° C./minute and is finally subjected to a second temperature rise passing from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

By way of pasty compounds, mention may be made of synthetic fatty substances and fatty substances of plant origin. The latter can be obtained by synthesis from starting materials of plant origin.

The solid fatty substance is advantageously chosen from:
lanolin and derivatives thereof,
polyol ethers chosen from pentaerythrityl ethers of a polyalkylene glycol, fatty alcohol ethers of a sugar, and mixtures thereof, the pentaerythrityl ether of polyethylene glycol comprising 5 oxyethylene units (5 OE) (CTFA name: PEG-5 Pentaerythrityl Ether), polypropylene glycol pentaerythrityl ether comprising 5 oxypropylene (5 OP) units (CTFA name: PPG-5 Pentaerythrityl Ether), and mixtures thereof, and more especially the PEG-5 Pentaerythrityl Ether, PPG-5 Pentaerythrityl Ether and soybean oil mixture sold under the Lanolide name by Vevy, which is a mixture in which the constituents are in a 46/46/8 ratio by weight: 46% PEG-5 Pentaerythrityl ether, 46% PPG-5 Pentaerythrityl ether and 8% soybean oil,
polymeric or non-polymeric silicone compounds,
polymeric or non-polymeric fluorinated compounds,
vinyl polymers, especially:
olefin homopolymers and copolymers,
hydrogenated diene homopolymers and copolymers,
linear or branched homopolymer or copolymer oligomers of alkyl (meth)acrylates preferably bearing a $C_8$-$C_{30}$ alkyl group, homopolymer and copolymer oligomers of vinyl esters bearing $C_8$-$C_{30}$ alkyl groups, homopolymer and copolymer oligomers of vinyl ethers containing $C_8$-$C_{30}$ alkyl groups, liposoluble polyethers resulting from polyetherification between one or more $C_2$-$C_{100}$ and preferably $C_2$-$C_{50}$ diols, esters, and/or mixtures thereof.

The solid fatty substance may be a polymer, in particular a hydrocarbon-based polymer. Among the liposoluble polyethers that are particularly preferred are copolymers of ethylene oxide and/or of propylene oxide with 06-030 long-chain alkylene oxides, more preferably such that the weight ratio of the ethylene oxide and/or of the propylene oxide to the alkylene oxides in the copolymer is from 5:95 to 70:30. In this family, mention will be made especially of the copolymers such as long-chain alkylene oxides arranged in blocks with an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are especially preferred:
- esters of a glycerol oligomer, especially diglycerol esters, in particular condensates of adipic acid and of glycerol, for which some of the hydroxyl groups of the glycerols have reacted with a mixture of fatty acids such as stearic acid, capric acid, isostearic acid and 12-hydroxystearic acid, especially such as the products sold under the brand name Softisan 649 by the company Sasol,
- the arachidyl propionate sold under the brand name Waxenol 801 by Alzo,
- phytosterol esters,
- fatty acid triglycerides and derivatives thereof,
- pentaerythritol esters,
- esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleate (Plandool G), phytosteryl dilinoleyl dimer dilinoleate (Lusplan PI-DA, Lusplan PHY/IS-DA), phytosteryl/isostearyl/cetyl/stearyl/behenyl dimer dilinoleate (Plandool H or Plandool S), and mixtures thereof,
- hydrogenated soybean oil, hydrogenated coconut oil, hydrogenated rape seed oil, mixtures of hydrogenated vegetable oils such as the mixture of hydrogenated soybean, coconut, palm and rapeseed vegetable oil, for example the mixture sold under the reference Akogel® by the company AarhusKarlshamn (INCI name: Hydrogenated Vegetable Oil),
- shea butter, in particular the product of which the INCI name is *Butyrospermum parkii* Butter, such as the product sold under the reference Sheasoft® by the company AarhusKarlshamn,
- cocoa butter, in particular the product which is sold under the name CT Cocoa Butter Deodorized by the company Dutch Cocoa BV or the product which is sold under the name Beurre De Cacao NCB HD703 758 by the company Barry Callebaut,
- shorea butter, in particular the product which is sold under the name Dub Shorea T by the company Stearinerie Dubois, and mixtures thereof.

According to one embodiment, the composition may comprise from 0.5% to 30% by weight of pasty compounds relative to the total weight of the composition.

The waxes that may be used in a composition according to the invention are chosen from waxes that are solid at ambient temperature, of animal, plant, mineral or synthetic origin, and mixtures thereof. They may be hydrocarbon-based, fluoro and/or silicone waxes.

Examples that may especially be mentioned include hydrocarbon-based waxes, such as natural beeswax (or bleached beeswax), synthetic beeswax, carnauba wax, rice bran wax, such as the product sold under the reference NC 1720 by the company Cera Rica Noda, candelilla wax, such as the product sold under the reference SP 75 G by the company Strahl & Pitsch, microcrystalline waxes, for instance the microcrystalline waxes of which the melting point is above 85° C., such as the products HI-MIC® 1070, 1080, 1090 and 3080 sold by the company Nippon Seiro, ceresins or ozokerites, for instance isoparaffins of which the melting point is below 40° C., such as the product EMW-0003 sold by the company Nippon Seiro, α-olefin oligomers, such as the Performa V® 825, 103 and 260 polymers sold by the company New Phase Technologies; ethylene/propylene copolymers, such as Performalene® EP 700, polyethylene waxes (preferably having a molecular weight of between 400 and 600), Fischer-Tropsch waxes.

The other solid fatty substances that may be present in the fatty phase are, for example, fatty acids comprising from 8 to 30 carbon atoms, for instance stearic acid, lauric acid or palmitic acid; fatty alcohols comprising from 8 to 30 carbon atoms, for instance stearyl alcohol or cetyl alcohol and mixtures thereof (cetearyl alcohol).

According to one embodiment, the composition may comprise from 0.5% to 20% by weight and preferably from 0.5% to 10% by weight of wax relative to the total weight of the composition.

The fatty phase of the composition in accordance with the invention can also comprise at least one oil. The oil(s) present in the composition may be volatile or non-volatile.

The term "oil" is intended to mean any fatty substance that is in liquid form at ambient temperature (25° C.) and at atmospheric pressure.

The volatile or non-volatile oils may be hydrocarbon-based oils, especially of animal or plant origin, synthetic oils, silicone oils or fluoro oils, or mixtures thereof.

For the purposes of the present invention, the term "silicone oil" is intended to mean an oil comprising at least one silicon atom, and especially at least one Si—O group.

The term "hydrocarbon-based oil" is intended to mean an oil mainly containing hydrogen and carbon atoms and possibly oxygen, nitrogen, sulfur and/or phosphorus atoms.

The term "fluoro oil" is intended to mean an oil comprising at least one fluorine atom and especially at least one perfluorinated chain.

Non-Volatile Oils

For the purposes of the present invention, the term "non-volatile oil" is intended to mean an oil with a vapour pressure of less than 0.13 Pa (0.01 mmHg).

The non-volatile oils may be chosen especially from non-volatile hydrocarbon-based oils, which may be fluorinated, and/or silicone oils.

As non-volatile hydrocarbon-based oil that are suitable for use in the invention, mention may be made especially of:
- hydrocarbon-based oils of animal origin,
- hydrocarbon-based oils of plant origin such as phytostearyl esters, such as phytostearyl oleate, phytostearyl isostearate and lauroyl/octyl-dodecyl/phytostearyl glutamate, for example sold under the name Eldew PS203 by Ajinomoto, triglycerides constituted of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides, for instance those sold by the company Stéarineries Dubois or those sold under the names Miglyol 810®, 812° and 818° by the company Dynamit Nobel; the refined vegetable perhydrosqualene sold under the name Fitoderm by the company Cognis;

hydrocarbon-based oils of mineral or synthetic origin, for instance:
  synthetic ethers containing from 10 to 40 carbon atoms, linear or branched hydrocarbons of mineral or synthetic origin, such as petroleum jelly, polydecenes, hydrogenated polyisobutene such as Parleam, and squalane, and mixtures thereof, and in particular hydrogenated polyisobutene;
  synthetic esters, such as the oils of formula $R_1COOR_2$, in which $R_1$ represents the residue of a linear or branched fatty acid comprising from 1 to 40 carbon atoms and $R_2$ represents an especially branched hydrocarbon-based chain containing from 1 to 40 carbon atoms, with the proviso that $R_1+R_2$ is ≥10.

The esters may be chosen especially from especially fatty acid esters, for instance:
  cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol 2-diethylhexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;
  polyol esters and pentaerythrityl esters, for instance dipentaerythrityl tetrahydroxystearate/tetraisostearate;
  esters of diol dimers and of diacid dimers, such as Lusplan DD-DA5® and Lusplan DD-DA7® sold by Nippon Fine Chemical and described in patent application FR 0302809,
  fatty alcohols that are liquid at ambient temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol;
  higher fatty acids such as oleic acid, linoleic acid and linolenic acid, and mixtures thereof; and
  dialkyl carbonates, the two alkyl chains possibly being identical or different, such as the dicaprylyl carbonate sold under the name Cetiol CC® by Cognis;
  non-volatile silicone oils, for instance non-volatile polydimethylsiloxanes (PDMSs), polydimethylsiloxanes comprising alkyl or alkoxy groups that are on the side and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof;
and mixtures thereof.

Volatile Oils

For the purposes of the present invention, "volatile oil" is intended to mean an oil (or non-aqueous medium) that is capable of evaporating on contact with the skin in less than one hour, at ambient temperature and at atmospheric pressure. The volatile oil is a volatile cosmetic oil, which is liquid at ambient temperature, especially having a non-zero vapour pressure, at ambient temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile hydrocarbon-based oils may be chosen from hydrocarbon-based oils containing from 8 to 16 carbon atoms.

The term "hydrocarbon-based oil" is intended to mean an oil formed essentially from, or even constituted of, carbon and hydrogen atoms, and possibly oxygen, nitrogen, sulfur and/or phosphorus atoms, and containing no silicon or fluorine atoms; it may contain ester, ether, amine or amide groups.

The volatile hydrocarbon-based oil(s) can in particular be chosen from volatile branched esters, volatile branched alkanes, volatile linear alkanes, and mixtures thereof.

The compositions according to the invention can comprise one or more branched $C_8$-$C_{16}$ esters, such as isohexyl neopentanoate, isoamyl esters such as isoamyl laurate, or else isononyl isononanoate.

The composition according to the invention may contain one or more volatile branched alkanes. The expression "one or more volatile branched alkanes" is intended to mean, without preference, "one or more volatile branched alkane oils".

As volatile branched alkanes, mention may particularly be made of $C_8$—C branched alkanes, such as $C_8$-$C_{16}$ isoalkanes (also known as isoparaffins), isododecane (also known as 2,2,4,4,6-pentamethylheptane), isodecane, isohexadecane, and for example the oils sold under the trade names Isopar® by Exxon Mobil or Permethyl® by Presperse. Preferably, the volatile hydrocarbon-based oil containing from 8 to 16 carbon atoms is chosen from isododecane, isodecane and isohexadecane, and mixtures thereof, and is in particular isododecane.

The composition according to the invention may contain one or more volatile linear alkanes. The term "one or more volatile linear alkanes" is intended to mean, without preference, "one or more volatile linear alkane oils".

A volatile linear alkane that is suitable for the invention is liquid at ambient temperature (about 25° C.) and at atmospheric pressure (760 mmHg).

A "volatile linear alkane" that is suitable for the invention is intended to mean a cosmetic linear alkane, which is capable of evaporating on contact with the skin in less than one hour, at ambient temperature (25° C.) and atmospheric pressure (760 mmHg, i.e. 101 325 Pa), which is liquid at ambient temperature, in particular having an evaporation rate ranging from 0.01 to 15 mg/cm$^2$/min, at ambient temperature (25° C.) and atmospheric pressure (760 mmHg).

Preferably, the "volatile linear alkanes" that are suitable for the invention have an evaporation rate ranging from 0.01 to 3.5 mg/cm$^2$/min, at ambient temperature (25° C.) and atmospheric pressure (760 mmHg).

Preferably, the "volatile linear alkanes" that are suitable for the invention have an evaporation rate ranging from 0.01 to 1.5 mg/cm$^2$/min, at ambient temperature (25° C.) and atmospheric pressure (760 mmHg).

More preferably, the "volatile linear alkanes" that are suitable for the invention have an evaporation rate ranging from 0.01 to 0.8 mg/cm$^2$/min, at ambient temperature (25° C.) and atmospheric pressure (760 mmHg).

Even more preferably, the "volatile linear alkanes" that are suitable for the invention have an evaporation rate ranging from 0.01 to 0.3 mg/cm$^2$/min, at ambient temperature (25° C.) and atmospheric pressure (760 mmHg).

Even more preferably, the "volatile linear alkanes" that are suitable for the invention have an evaporation rate ranging from 0.01 to 0.12 mg/cm$^2$/min, at ambient temperature (25° C.) and atmospheric pressure (760 mmHg).

The evaporation rate of a volatile alkane in accordance with the invention (and more generally of a volatile solvent) may in particular be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 m$^3$ which is temperature-regulated (25° C.) and hygrometry-regulated (50% relative humidity).

The liquid is allowed to evaporate freely, without stirring it, while providing ventilation by means of a fan (Papst-Motoren, reference 8550 N, rotating at 2700 rpm) placed vertically above the crystallizing dish containing the volatile hydrocarbon-based solvent, the blades being directed towards the crystallizing dish, at a distance of 20 cm relative to the bottom of the crystallizing dish.

The weight of volatile hydrocarbon-based solvent remaining in the crystallizing dish is measured at regular time intervals.

The evaporation profile of the solvent is then obtained by plotting the curve of the amount of product evaporated (in mg/cm$^2$) as a function of the time (in min).

The evaporation rate is then calculated, which corresponds to the tangent to the origin of the curve obtained. The evaporation rates are expressed in mg of volatile solvent evaporated per unit of surface area (cm$^2$) and per unit of time (minutes).

According to one preferred embodiment, "the volatile linear alkanes" that are suitable for the invention have a non-zero vapour pressure (also known as saturation vapour pressure), at ambient temperature, in particular a vapour pressure ranging from 0.3 Pa to 6000 Pa.

Preferably, the "volatile linear alkanes" that are suitable for the invention have a vapour pressure ranging from 0.3 to 2000 Pa, at ambient temperature (25° C.).

Preferably, the "volatile linear alkanes" that are suitable for the invention have a vapour pressure ranging from 0.3 to 1000 Pa, at ambient temperature (25° C.).

More preferably, the "volatile linear alkanes" that are suitable for the invention have a vapour pressure ranging from 0.4 to 600 Pa, at ambient temperature (25° C.).

Preferably, the "volatile linear alkanes" that are suitable for the invention have a vapour pressure ranging from 1 to 200 Pa, at ambient temperature (25° C.).

More preferably, the "volatile linear alkanes" that are suitable for the invention have a vapour pressure ranging from 3 to 60 Pa, at ambient temperature (25° C.).

According to one embodiment, a volatile linear alkane that is suitable for the invention may have a flash point that is within the range from 30 to 120° C. and more particularly from 40 to 100° C. The flash point is in particular measured according to standard ISO 3679.

According to one embodiment, an alkane that is suitable for the invention may be a volatile linear alkane comprising from 8 to 16 carbon atoms.

According to one advantageous embodiment, the "volatile linear alkanes" that are suitable for the invention have an evaporation rate, as defined above, ranging from 0.01 to 3.5 mg/cm$^2$/minute, at ambient temperature (25° C.) and atmospheric pressure (760 mmHg), and comprise from 8 to 16 carbon atoms.

A volatile linear alkane that is suitable for the invention may advantageously be of plant origin.

Such an alkane may be obtained, directly or in several steps, from a plant raw material, such as an oil, a butter, a wax, etc.

As examples of alkanes that are suitable for the invention, mention may be made of the alkanes described in patent applications by the company Cognis WO 2007/068 371 or WO 2008/155 059 (mixtures of different alkanes differing by at least one carbon). These alkanes are obtained from fatty alcohols, which are themselves obtained from coconut oil or palm oil.

As examples of linear alkanes that are suitable for the invention, mention may be made of n-octane (C8), n-nonane (C9), n-decane (C10), n-undecane (C11), n-dodecane (C12), n-tridecane (C13), n-tetradecane (C14), hexadecane (C16) and mixtures thereof. According to a particular embodiment, the volatile linear alkane is chosen from n-nonane, n-undecane, n-dodecane, n-tridecane and n-tetradecane, and mixtures thereof.

The volatile linear alkane may be used alone.

Alternatively or preferentially, a mixture of at least two different volatile linear alkanes, differing from each other by a carbon number n of at least 1, in particular differing from each other by a carbon number of 1 or 2, may be used.

According to a first embodiment, a mixture of at least two different volatile linear alkanes comprising from 10 to 16 carbon atoms and differing from each other by a carbon number of at least 1 may be used. By way of examples, mention may especially be made of the mixtures of volatile linear alkanes C10/C11, C11/C12, and C12/C13.

According to another embodiment, a mixture of at least two different volatile linear alkanes comprising from 10 to 16 carbon atoms and differing from each other by a carbon number of at least 2, is used. By way of examples, mention may in particular be made of the mixtures of volatile linear alkanes C10/C12, and C12/C14, for an even carbon number n and the mixture C11/C13 for an odd carbon number n.

According to one preferred embodiment, a mixture of at least two different volatile linear alkanes comprising from 10 to 16 carbon atoms and differing from each other by a carbon number of at least 2, and in particular a mixture of C11/C13 volatile linear alkanes or a mixture of C12/C14 volatile linear alkanes, is used.

Other mixtures combining more than two volatile linear alkanes according to the invention, for instance a mixture of at least three different volatile linear alkanes comprising from 8 to 16 carbon atoms and differing from each other by a carbon number of at least 1, also form part of the invention, but the mixtures of two volatile linear alkanes according to the invention are preferred (binary mixtures), said two volatile linear alkanes preferably representing more than 95% and better still more than 99% by weight of the total content of volatile linear alkanes in the mixture. According to one particular embodiment of the invention, in a mixture of volatile linear alkanes, the volatile linear alkane having the smallest carbon number is predominant in the mixture.

According to another embodiment of the invention, a mixture of volatile linear alkanes in which the volatile linear alkane having the largest carbon number is predominant in the mixture is used.

As examples of mixtures that are suitable for the invention, mention may be made in particular of the following mixtures:

from 50% to 90% by weight, preferably from 55% to 80% by weight and more preferentially from 60% to 75% by weight of a $C_n$ volatile linear alkane with n ranging from 8 to 16, from 10% to 50% by weight, preferably from 20% to 45% by weight and preferably from 24% to 40% by weight of $C_{n+x}$ volatile linear alkane with x greater than or equal to 1, preferably x=1 or x=2, with n+x between 8 and 16, relative to the total weight of the alkanes in said mixture.

In particular, said mixture of alkanes according to the invention contains:

less than 2% by weight and preferably less than 1% by weight of branched hydrocarbons, and/or less than 2% by weight and preferably less than 1% by weight of aromatic hydrocarbons, and/or less than 2% by weight, preferably less than 1% by weight and preferentially less than 0.1% by weight of unsaturated hydrocarbons in the mixture.

More particularly, a volatile linear alkane that is suitable for the invention may be used in the form of an n-undecane/n-tridecane mixture.

In particular, use will be made of a mixture of volatile linear alkanes comprising:

from 55% to 80% by weight and preferably from 60% to 75% by weight of a C11 volatile linear alkane (n-undecane), from 20% to 45% by weight and preferably from 24% to 40% by weight of a C13 volatile linear alkane (n-tridecane), relative to the total weight of the alkanes in said mixture.

According to one particular embodiment, the mixture of alkanes is an n-undecane/n-tridecane mixture. In particular, such a mixture may be obtained according to Example 1 or Example 2 of WO 2008/155059.

By way of examples of volatile hydrocarbon-based oils that may be used in the invention, mention may be made of:

n-dodecane, such as that which is sold under the reference Parafol 12-97 by Sasol;

n-tetradecane, such as that which is sold under the reference Parafol 14-97 by Sasol;

a mixture of n-dodecane and n-tetradecane;

isododecane (C12) such as that which is sold by the company Ineos;

a mixture of $C_{15}$-$C_{16}$ branched alkanes, for example that which is sold by the company SEPPIC under the name Emogreen L15;

a mixture of $C_{13}$-$C_{15}$ linear and/or branched alkanes, for example that which is sold by the company SEPPIC under the name Emosmart L15.

Volatile oils that may also be used include volatile silicones, such as, for example, volatile linear or cyclic silicone oils, especially those having a viscosity ≤8 centistokes ($8 \times 10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. As volatile silicone oil that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof. Volatile fluoro oils such as nonafluoromethoxybutane or perfluoromethylcyclopentane, and mixtures thereof, may also be used.

It is also possible to use a mixture of the oils mentioned above.

The various fatty substances as previously defined may be chosen in a varied manner by those skilled in the art so as to prepare a composition having the desired properties, for example in terms of consistency or texture.

According to one particular embodiment of the invention, the fatty phase of the composition comprises at least one oil. Preferably, the composition in accordance with the invention comprises at least one volatile hydrocarbon-based oil.

According to one embodiment, the composition comprises from 0.5% to 70% by weight, preferably from 0.5% to 50% by weight, of oil(s), relative to the total weight of the composition.

Aqueous Phase

The composition in accordance with the invention comprises at least one aqueous phase. The aqueous phase comprises at least water. According to the galenical form of the composition, the amount of aqueous phase may range from 0.1% to 99% by weight, preferably from 0.5% to 98% by weight, better still from 30 to 95% by weight and even better still from 40 to 95% by weight relative to the total weight of the composition.

The amount of water may represent all or a portion of the aqueous phase and it is generally at least 30% by weight relative to the total weight of the composition, preferably at least 50% by weight, better still at least 60% by weight.

The aqueous phase may comprise at least one organic solvent that is water-miscible at ambient temperature (25° C.), for instance linear or branched monoalcohols containing from 2 to 6 carbon atoms, such as ethanol, propanol, butantol, isopropanol, isobutanol, pentanol or hexanol; polyols especially containing from 2 to 20 carbon atoms, preferably from 2 to 6 carbon atoms, such as glycerine, propylene glycol, isoprene glycol, butylene glycol, propylene glycol, pentylene glycol, hexylene glycol, dipropylene glycol, diethylene glycol, triethylene glycol, glycerol, sorbitol, and mixtures thereof.

In a known manner, all the compositions of the invention may comprise one or more of the adjuvants that are common in cosmetics and dermatology: additional surfactants (different than the gemini surfactants as previously described), additional hydrophilic gelling agents and/or thickeners; lipophilic gelling agents and/or thickeners; moisturizers; emollients; hydrophilic or lipophilic active agents; free-radical scavengers; sequestrants; antioxidants; preservatives; basifying or acidifying agents; fragrances; film-forming agents; fillers; and mixtures thereof.

The amounts of these various adjuvants are those conventionally used in the fields under consideration. In particular, the amounts of active agents vary according to the desired aim and are those conventionally used in the fields under consideration, for example from 0.1 to 20% and preferably from 0.5 to 10% by weight of the total weight of the composition. When the composition comprises additional surfactants, the latter are preferably present in the composition in a proportion of active material ranging from 0.1% to 30% by weight, and preferably from 0.2% to 20% by weight, relative to the total weight of the composition.

Active Agents

Non-limiting examples of active agents that may be mentioned include ascorbic acid and derivatives thereof such as 5,6-di-O-dimethylsilyl ascorbate (sold by the company Exsymol under the reference PRO-AA), the potassium salt of dl-alpha-tocopheryl-2I-ascorbyl phosphate (sold by the company Senju Pharmaceutical under the reference Sepivital EPC), magnesium ascorbyl phosphate, sodium ascorbyl phosphate (sold by the company Roche under the reference Stay-C 50); phloroglucinol; enzymes; and mixtures thereof. According to a preferred embodiment of the invention, use is made, among oxidation-sensitive hydrophilic active agents, of ascorbic acid. The ascorbic acid may be of any nature. Thus, it may be of natural origin in powder form or in the form of orange juice, preferably orange juice concentrate. It may also be of synthetic origin, preferably in powder form.

As other active agents that can be used in the composition of the invention, mention may be made, for example, of moisturising agents, such as protein hydrolysates and polyols, for instance glycerol, glycols, for instance polyethylene glycols; natural extracts; anti-inflammatories; oligomeric proanthocyanidins; vitamins such as vitamin A (retinol), vitamin E (tocopherol), vitamin B5 (panthenol), vitamin B3 (niacinamide), derivatives of these vitamins (in particular esters) and mixtures thereof; urea; caffeine; depigmenting agents such as kojic acid, hydroquinone and caffeic acid; salicylic acid and derivatives thereof; alpha-hydroxy acids, such as lactic acid and glycolic acid and derivatives thereof; retinoids, such as carotenoids and vitamin A derivatives; hydrocortisone; melatonin; extracts of algae, of fungi, of plants, of yeasts, of bacteria; steroids; antibacterial active agents, such as 2,4,4'-trichloro-2'-hydroxy diphenyl ether (or triclosan), 3,4,4'-trichlorocarbanilide (or triclocarban) and the acids indicated above, and in particular salicylic acid and derivatives thereof; matting agents, for instance fibres; tensioning agents; UV-screening agents, in particular organic UV-screening agents; and mixtures thereof.

Needless to say, those skilled in the art will take care to select the optional adjuvant(s) added to the composition according to the invention such that the advantageous properties intrinsically associated with the composition in accordance with the invention are not, or are not substantially, adversely affected by the envisaged addition.

The compositions in accordance with the invention may for example be in the form of a cream or a milk.

The compositions according to the invention may in particular be in the form of a vapourizable emulsion applied to the skin or the hair in the form of fine particles by means of pressurization devices. The devices in accordance with the invention are well known to those skilled in the art and comprise non-aerosol pumps or "atomizers", aerosol containers comprising a propellant and aerosol pumps using compressed air as propellant. These devices are in particular described in U.S. Pat. Nos. 4,077,441 and 4,850,517.

The compositions in accordance with the invention that are packaged in aerosol form generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The compositions may also be impregnated onto supports such as wipes, or they may be packaged as lotions in a bottle with a reducing agent.

The examples that follow will allow the invention to be understood more clearly, without, however, being limiting in nature. The amounts indicated are weight percentages of raw materials, unless otherwise mentioned. The names of the compounds are given as the chemical names or the INCI names.

EXAMPLES

Example of Lipophilic Polymer Synthesis

Determination of the Molecular Weight by Gel Permeation Chromatography (GPC):

The sample is prepared by preparing a solution of the polymer at 10 mg/ml in tetrahydrofuran. The sample is placed in an oven at 54° C. for 10 minutes and then in an oscillating shaker for 60 minutes in order to assist with the dissolution. After visual inspection, the sample appears to be totally dissolved in the solvent.

The sample prepared was analysed using two polypore 300×7.5 mm columns (manufactured by Agilent Technologies), a Waters 2695 chromatographic system, a tetrahydrofuran mobile phase and detection by refractive index. The sample was filtered through a 0.45 µm nylon filter, before being injected into the liquid chromatograph. The standards used for the calibration are the Easi Vial narrow polystyrene (PS) standards from Agilent Technologies.

Polystyrene standards ranging from 2 520 000 to 162 Daltons were used for the calibration.

The system is equipped with a PSS SECcurity 1260 RI detector. The polystyrene calibration curve was used to determine the average molecular weight. The recording of the diagrams and the determination of the various molecular weights was carried out by the Win GPC Unichrom 81 program.

Determination of the Melting Point by Differential Scanning Calorimetry (or DSC):

This method describes the general procedure for determining the melting point of polymers by differential scanning calorimetry. This method is based on the standards ASTM E791 and ASTM D 34182 and the DSC calibration is carried out according to the standard ASTM E 9672.

Behenyl Acrylate/2-hydroxyethyl Acrylate Copolymer (Polymer 1):

In a 4-necked flask equipped with side-blade mixer, an internal thermometer, two funnels, a reflux condenser, and an extension for two other necks, 175 g of behenyl acrylate, 25 g of 2-hydroxyethyl acrylate and 0.4 g of 2,2'-azobis(2-methylbutyronitrile (Akzo Nobel)) were added, over the course of 60 minutes at 80° C., to 40 g of isopropanol, with stirring, after having removed the oxygen from the system by means of a nitrogen flush for 20 minutes.

The mixture was stirred at 80° C. for 3 hours. The solvent was then eliminated by vacuum distillation, then 1 g of dilauryl peroxide was added and the reaction was continued for 60 minutes at 110° C. The step was repeated. The mixture was then cooled to 90° C. and a jet of demineralized water was added, then the mixture was stirred. The water was eliminated by vacuum distillation.

Molecular weight: Mn=7300 g/mol, Mw=21000, Mw/Mn=2.8

Melting point: 65° C.

Formulation Examples

For each composition, the viscosity was measured and/or the stability over time was studied at various temperatures and/or the sensory aspect was evaluated during and after its application to the skin.

Viscosity Measurement

The viscosity measurement is generally carried out at 25° C., using a Rheomat RM180® viscometer equipped with a No. 3 spindle, the measurement being carried out after 10 minutes of rotation of the spindle in the composition (after which time stabilization of the viscosity and of the speed of rotation of the spindle are observed), at a shear rate of 200 $s^{-1}$.

Study of the Stability Over Time at Various Temperatures

The stability is studied over time by observing the change in the composition with regard to its macroscopic appearance, its microscopic appearance, and the change in viscosity and pH values, at various temperatures such as ambient temperature (AT), 4° C. or 45° C.

Protocol for Evaluating the Tack, the Shininess and the Greasiness

The tacky, shiny and greasy effects of the compositions are evaluated by a panel of sensory experts made up of 5 to 20 individuals according to the examples. Each composition is applied to the forearm at the dose of 2 mg/cm$^2$. The product was spread by circular movements until it had penetrated (approximately 30 seconds). The tacky, shiny and greasy effects are evaluated after 2 minutes of drying, by applying the back of the hand to the treated area, according to a scale ranging from 1 to 15 in which 1 constitutes a reference that is not very tacky or not very shiny or not very greasy, and 15 constitutes a reference that is very tacky or very shiny or very greasy.

Comparative Example 1

Emulsions 1 to 9 of oil-in-water type as described below were prepared.

| Composition | 1 invention | 2 invention | 3 invention | 4 invention | 5 invention |
|---|---|---|---|---|---|
| Preservative(s) | 0.7 | 0.7 | 0.7 | 0.7 | 0.7 |
| Disodium ethylenediaminetetraacetic acid dihydrate | 0.1 | 0.1 | 0.1 | 0.1 | 0.1 |
| Polymer 1 as previously synthesized | 3 SM (3 AM) | 3 SM (3 AM) | 3 SM (3 AM) | 3 SM (3 AM) | 3 SM (3 AM) |
| Ethoxylated methacrylic acid/methyl acrylate/dimethyl-meta-isopropenyl benzyl isocyanate alcohol terpolymer (Viscophobe DB 1000 from Amerchol) | 2.6 SM (0.6 AM) | — | — | — | — |
| Oxyethylenated methacrylic acid/ethyl acrylate/behenyl methacrylate terpolymer (25 OE) as an aqueous emulsion (Aculyn 28 Polymer ® - Rohm and Haas) | — | 3 SM (0.6 AM) | — | — | — |
| Acrylates/C10-C30 Alkyl Acrylate Crosspolymer (Carbopol Ultrez 20 Polymer from Lubrizol) | — | — | 0.7 SM (0.6 AM) | — | — |
| Acrylic acid/stearyl methacrylate copolymer polymerized in an ethyl acetate/cyclohexane mixture (Pemulen TR-1 Polymer from Lubrizol) | — | — | — | 0.6 SM (0.6 AM) | — |
| Crosslinked acrylic acid/alkyl acrylate polymer (Pemulen TR-2 Polymer from Lubrizol) | — | — | — | — | 0.6 SM (0.6 AM) |
| Glycerol | 8 | 8 | 8 | 8 | 8 |
| Isononyl isononanoate | 20 | 20 | 20 | 20 | 20 |
| 1,2-Octanediol | 0.5 | 0.5 | 0.5 | 0.5 | 0.5 |
| Triethanolamine | 0.25 | 0.25 | 0.5 | 0.5 | 0.5 |
| Water | qs 100 | qs 100 | qs 100 | qs 100 | qs 100 |

| Composition | 6 (comparative) | 7 (comparative) |
|---|---|---|
| Preservative(s) | 0.7 | 0.7 |
| Disodium ethylenediaminetetraacetic acid dihydrate | 0.1 | 0.1 |
| Polymer 1 as previously synthesized | 3 SM (3 AM) | 3 SM (3 AM) |
| Polyurethane-62 (and) trideceth-6 (Avalure Flex 6 Polymer from Lubrizol) | 0.7 SM (0.6 AM) | — |
| Carboxyvinyl polymer synthesized in the ethyl acetate/cyclohexane mixture (Carbopol 980 Polymer from Lubrizol) | — | 0.6 SM (0.6 AM) |
| Glycerol | 8 | 8 |
| Isononyl isononanoate | 20 | 20 |
| 1,2-Octanediol | 0.5 | 0.5 |
| Triethanolamine | — | 0.5 |
| Water | qs 100 | qs 100 |

In the tables above, SM signifies starting material and AM signifies active material.

Compositions 1 to 7 were prepared according to the following procedure: Heat the fatty phase containing the oil and the lipophilic polymer at 70° C. until the polymer has completely melted and dissolved.

In another container, disperse, in the aqueous phase, containing the water, the preservatives and the glycerol, and the chosen hydrophilic gelling polymer and neutralize it if required using the base, then heat said phase to 70° C.

Incorporate, with rigourous stirring (rotor/stator type), the oily phase (at 70° C.) into the aqueous phase (at 70° C.) and cool the resulting emulsion to 25° C.

The results obtained are shown in the table below.

| Composition | 1 (invention) | 2 (invention) | 3 (invention) | 4 (invention) | 5 (invention) |
|---|---|---|---|---|---|
| pH at 24 h | 5.8 | 5.9 | 5.5 | 5.5 | 5.6 |
| Viscosity at 24 h in Pa·s | 1.03 | 1.45 | 3.41 | 2.20 | 1.53 |
| Macroscopic appearance at 24 h | Smooth white cream, complies | Smooth white cream, complies | Smooth white cream, complies | Smooth white cream, complies | Smooth white cream, complies |
| Microscopic appearance at 24 h | Emulsion | Emulsion | Emulsion | Emulsion | Emulsion |
| Change over time | No change, neither macroscopic nor microscopic, after 2 months at AT and at 45° C., pH and viscosity stable | No change, neither macroscopic nor microscopic, after 2 months at AT and at 45° C., pH and viscosity stable | No change, neither macroscopic nor microscopic, after 2 months at AT and at 45° C., pH and viscosity stable | No change, neither macroscopic nor microscopic, after 2 months at AT and at 45° C., pH and viscosity stable | No change, neither macroscopic nor microscopic, after 2 months at AT and at 45° C., pH and viscosity stable |
| Sensory aspect | Non-greasy non-tacky | Non-greasy non-tacky | Non-greasy non-tacky | Non-greasy non-tacky | Non-greasy non-tacky |

| Composition | 6 (comparative) | 7 (comparative) |
|---|---|---|
| pH at 24 h | 4.6 | Not measurable, no emulsion |
| Viscosity at 24 h in Pa·s | 0.13 | Not measurable, no emulsion |
| Macroscopic appearance at 24 h | Ultra-fluid, white, smooth | No emulsion, large clumps |
| Microscopic appearance at 24 h | Emulsion | No emulsion, large clumps |
| Change over time | Creaming after 1 week at AT | No emulsion, large clumps |
| Sensory aspect | Not stable after one week, therefore not of interest in the evaluation | Not measurable, no emulsion |

Compositions 1 to 5 comprising an anionic acrylic copolymer as hydrophilic gelling polymer (composition in accordance with the invention) are stable over time and have good sensory properties, in particular a non-tacky and non-greasy effect on the skin.

Compositions 6 and 7 comprising a hydrophilic gelling polymer which is not an anionic acrylic copolymer (comparative composition) are either unstable over time or do not make it possible to obtain an emulsion. The sensory properties cannot be evaluated.

Comparative Example 2

Emulsions 8 to 15 of oil-in-water type as described below were prepared.

also the hydrophilic gelling polymer and neutralize it using the base (triethanolamine), then heat said phase to 70° C.

Incorporate, with rigourous stirring (rotor/stator type), the oily phase (at 70° C.) into the aqueous phase (at 70° C.) and cool the resulting emulsion to 25° C.

Composition 12 will be prepared according to the same process, but without using hydrophilic gelling polymer and without neutralization (triethanolamine).

Compositions 8 to 10 which comprise the combination of an anionic acrylic copolymer (Carbopol Aqua SF-1 Polymer from Lubrizol) and of a lipophilic polymer as claimed (Polymer 1) are in the form of fine emulsions and make it possible to obtain good sensory properties, in particular a non-tacky and non-greasy effect on the skin.

| Composition | 8 invention | 9 invention | 10 invention | 11 comparative | 12 comparative |
|---|---|---|---|---|---|
| Preservative(s) | 0.7 | 0.7 | 0.7 | 0.7 | 0.7 |
| Disodium ethylenediaminetetraacetic acid dihydrate | 0.1 | 0.1 | 0.1 | 0.1 | 0.1 |
| Polymer 1 as previously synthesized | 1 SM (1 AM) | 2 SM (2 AM) | 3 SM (3 AM) | — | 3 SM (3 AM) |
| Lightly crosslinked acrylic polymer in emulsion (Carbopol Aqua SF-1 polymer from Lubrizol) | 2 SM (0.6 AM) | 2 SM (0.6 AM) | 2 SM (0.6 AM) | 2 SM (0.6 AM) | — |
| Glycerol | 8 | 8 | 8 | 8 | 8 |
| Isononyl isononanoate | 20 | 20 | 20 | 20 | 20 |
| 1,2-Octanediol | 0.5 | 0.5 | 0.5 | 0.5 | 0.5 |
| Triethanolamine | 0.25 | 0.25 | 0.25 | 0.25 | — |
| Water | qs 100 | qs 100 | qs 100 | qs 100 | qs 100 |

| Composition | 13 (comparative) | 14 (comparative) | 15 (comparative) |
|---|---|---|---|
| Preservative(s) | 0.7 | 0.7 | 0.7 |
| Disodium ethylenediaminetetraacetic acid dihydrate | 0.1 | 0.1 | 0.1 |
| Poly(stearyl acrylate) (Intelimer IPA 13-1 from Evonik Materials Netherlands B.V.) | 1 SM (1 AM) | 2 SM (2 AM) | — |
| Poly(behenyl acrylate) (Intelimer IPA 13-6 from Evonik Materials Netherlands B.V.) | — | — | 3 SM (3 AM) |
| Lightly crosslinked acrylic polymer in emulsion (Carbopol Aqua SF-1 polymer from Lubrizol) | 2 SM (0.6 AM) | 2 SM (0.6 AM) | 2 SM (0.6 AM) |
| Polyurethane-62 (and) trideceth-6 (Avalure Flex 6 Polymer from Lubrizol) | — | 0.7 SM (0.6 AM) | — |
| Carboxyvinyl polymer synthesized in the ethyl acetate/cyclohexane mixture (Carbopol 980 Polymer from Lubrizol) | — | — | 0.6 SM (0.6 AM) |
| Glycerol | 8 | 8 | 8 |
| Isononyl isononanoate | 20 | 20 | 20 |
| 1,2-Octanediol | 0.5 | 0.5 | 0.5 |
| Triethanolamine | 0.25 | 0.25 | 0.25 |
| Water | qs 100 | qs 100 | qs 100 |

In the tables above, SM signifies starting material and AM signifies active material.

Compositions 8 to 11 and 13 to 15 were prepared according to the following procedure: Heat the fatty phase containing the oil and the lipophilic polymer at 70° C. until the polymer has completely melted and dissolved.

In another container, disperse, in the aqueous phase, containing the water, the preservatives and the glycerol, and Comparative composition 11 which comprises an anionic acrylic copolymer (Carbopol Aqua SF-1 Polymer from Lubrizol) alone is in the form of a fine emulsion but it has a greasy, oily feel when applied to the skin.

With comparative composition 12 which comprises a lipophilic polymer as claimed (Polymer 1) alone, it is not possible to obtain an emulsion, and the sensory properties cannot be measured.

Comparative compositions 13 and 14 which comprise the combination of an anionic acrylic copolymer (Carbopol Aqua SF-1 Polymer from Lubrizol) and of a lipophilic polymer other than those which are claimed (Intelimer IPA 13-1 from Evonik Materials Netherlands B.V.) are in the form of fine emulsions and make it possible to obtain sensory properties (tack, shininess, greasiness) which are not as good as the compositions in accordance with the invention.

With comparative composition 15 which comprises the combination of an anionic acrylic copolymer (Carbopol Aqua SF-1 Polymer from Lubrizol) and of a lipophilic polymer other than those which are claimed (Intelimer IPA 13-6 from Evonik Materials Netherlands B.V.), it is not possible to obtain an emulsion, and the sensory properties cannot be measured.

Illustrative Example 3: Anti-Ageing Cream with No Screening

Composition 16 as presented below was prepared.

| Phase | Composition | 16 (invention) |
|---|---|---|
| A1 | Water | 48.95 |
| A1 | Glycerol | 8 |
| A1 | Caprylyl glycol | 0.5 |
| A1 | Preservative(s) | 0.5 |
| A1 | Disodium ethylenediaminetetraacetic acid dihydrate | 0.1 |
| A2 | Lightly crosslinked acrylic polymer in emulsion (Carbopol Aqua SF-1 polymer from Lubrizol) | 2 |
| A3 | Water | 3 |
| A3 | Triethanolamine | 0.25 |
| B | Polydimethylsiloxane (viscosity: 5 cSt) (Belsil DM 5 plus from Wacker) | 5 |
| B | Hydrogenated isoparaffin (6-8 mol of isobutylene) | 5 |
| B | Isononyl isononanoate | 5 |
| B | Diisopropyl sebacate | 5 |
| B | Refined palm oil | 5 |
| B | Polymer 1 as previously synthesized | 3 |
| B | Vitamin E | 0.5 |
| C | Ethoxylated (25 EO) AMPS/stearyl methacrylate copolymer crosslinked with trimethylolpropane triacrylate (TMPTA), (Aristoflex HMS from Clariant) | 0.6 |
| D | Mixture of polydimethylsiloxane crosslinked with hexadiene/polydimethylsiloxane 5 cSt (Dow Corning 9041 Silicone Elastomer Blend from Dow Corning) | 2 |
| E | Methylsilanol/Silicate Cross polymer (NLK-506 from Takemoto Oil&Fat) | 3 |
| E | Crosslinked polydimethylsiloxane gum beads coated with silsesquioxane resin (92/8) (KSP 100 from Shin-Etsu) | 2 |
| F | Fragrance(s) | 0.6 |

Procedure

Composition 16 is prepared in the following manner:
1) Preparation and homogenization of phases A and B:
Heat the aqueous phase A1 to 75° C. with magnetic stirring.
Add phase A2 (Carbopol Aqua SF1 from Lubrizol) to the aqueous phase A1 using a deflocculating device.
Neutralize the mixture A1+A2 by adding phase A3 using a deflocculating device.
Reheat the aqueous phase A thus obtained, so as to maintain a temperature above 75° C. for the emulsion.
Heat the oily phase B to 75° C. with magnetic stirring.
2) Emulsification:
Pour the oily phase B into the aqueous phase A using an emulsifying device and homogenize for 10 minutes.
3) Pass through a Rayneri—deflocculating device and stop the heating.
4) Add phases C, D, E and F:
Add phase C below 45° C. using a deflocculating device and allow to swell for 20 to 30 minutes.
Cool to 25° C. with a water bath using a deflocculating device.
Starting from 35° C., add phases D, E and F using a deflocculating device.

Composition 16 thus obtained is a homogeneous, thick, white, fragranced cream which is smooth and shiny and which has a viscosity of 8 Pa·s and a pH of 6.55. It is in the form of a fine and regular emulsion, with clear edges.

Composition 16 is stable after two months at AT, 4° C. and 45° C. (macroscopic and microscopic appearances, viscosity, pH).

The sensory results obtained, evaluated with a panel of 19 individuals, are presented in the table below.

| Composition | 16 (invention) |
|---|---|
| Tacky finish (Score by sensory expert panel, out of 15; 1 = not very tacky; 15 = very tacky) | Tacky finish 0.5/15 |
| Shininess (Score by sensory expert panel, out of 15; 1 = not very shining; 15 = very shiny) | Shininess 2/15 |
| Greasy (Score by sensory expert panel, out of 15; 1 = not very greasy; 15 = very greasy) | Greasy 7.5/15 |

Composition 16 is non-tacky, non-shiny and non-greasy.

The invention claimed is:

1. A composition in the form of an emulsion comprising at least one hydrophilic gelling polymer chosen from anionic acrylic copolymers and at least one lipophilic polymer comprising monomeric units of formulae (A) and (B):

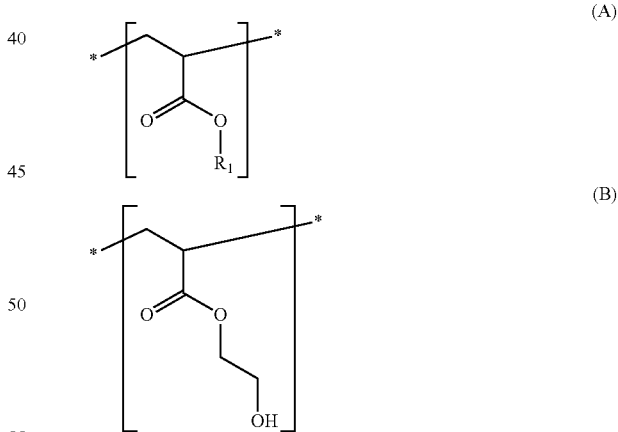

in which:
R$_1$, independently of one another, are chosen from alkyl or alkylene radicals;
with at least 60% by weight of the R$_1$ groups being behenyl radicals, the percentage by weight relating to the sum of all the R$_1$ groups present in the polymer;
the weight ratio of the sum of all the hydroxyethyl acrylate units to the sum of all the acrylate units bearing the R$_1$ group ranges from 1:30 to 1:1; and
the sum of the total of units (A) and (B) is at least 95% by weight of the total weight of the polymer;

the at least one lipophilic polymer having a number-average molecular weight Mn ranging from 2000 to 9000 g/mol.

2. The composition according to claim 1, in which the anionic acrylic copolymers are chosen from:

anionic acrylic copolymers derived from at least one unsaturated carboxylic acid or from at least one ester of an unsaturated carboxylic acid and of a monoalcohol comprising from 1 to 6 carbon atoms; or at least one anionic associative acrylic copolymer.

3. The composition according to claim 2, in which each of the anionic acrylic copolymers derived from at least one unsaturated carboxylic acid or from at least one ester of an unsaturated carboxylic acid and of a monoalcohol comprising from 1 to 6 carbon atoms comprises:

a monomeric unit corresponding to formula (I) below:

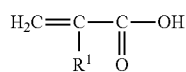

(I)

in which $R^1$ denotes H or $CH_3$ or $C_2H_5$, and a monomeric unit of formula (II) below:

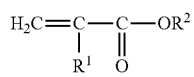

(II)

in which $R^1$ denotes H or $CH_3$ or $C_2H_5$, and $R^2$ denotes an alkyl group comprising from 1 to 6 carbon atoms.

4. The composition according to claim 2, in which the at least one anionic associative acrylic copolymer is chosen from:

(1) copolymers derived from the polymerization of:

(i) (meth)acrylic acid and (ii) a monomer of formula (III) below:

(III)

in which R' denotes H or $CH_3$, B denotes the ethyleneoxy group ($-CH_2-CH_2-O-$), n is zero or denotes an integer ranging from 1 to 100 and R denotes a hydrocarbon-based group chosen from an alkyl group, an arylalkyl group, an aryl group, an alkylaryl group or a cycloalkyl group comprising from 8 to 30 carbon atoms;

(2) associative polymers comprising at least one hydrophilic unit of α,β-monoethylenically unsaturated carboxylic acid and at least one hydrophobic unit of ($C_{10}$-$C_{30}$)alkyl ester of α,β-monoethylenically unsaturated carboxylic acid;

(3) acrylic terpolymers comprising:

(a) from 19.5% to 70% by weight of an α,β-monoethylenically unsaturated carboxylic acid containing from 3 to 5 carbon atoms, (b) from 20% to 80% by weight of a monomer chosen from $C_1$-$C_4$ alkyl (meth)acrylates and (c) from 0.5% to 60% by weight of a non-ionic urethane macromonomer of formula (VI) below:

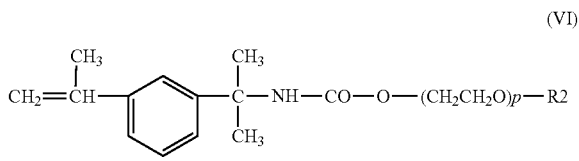

(VI)

in which p ranges from 6 to 150 and R2 is chosen from linear alkyl radicals comprising from 18 to 26 carbon atoms;

(4) copolymers of (a) an α,β-monoethylenically unsaturated carboxylic acid, (b) an ester of an α,β-monoethylenically unsaturated carboxylic acid and a polyoxyethylenated C12-C30 fatty alcohol and (c) an ester of an α,β-monoethylenically unsaturated carboxylic acid and a $C_1$-$C_4$ alcohol; or (5) copolymers of (a) (meth)acrylic acid, (b) crosslinked $C_1$-$C_4$ alkyl (meth)acrylate, (c) polyethylene glycol $C_{10}$-$C_{30}$ alkyl ether methacrylate containing 25 mol of ethylene oxide and (d) polyethylene glycol allyl ether containing 20 ethylene oxide units/polypropylene glycol containing 5 propylene oxide units.

5. The composition according to claim 4, in which the monomer of formula (III) is a monomer in which R' denotes H, n is equal to 10 and R denotes a stearyl (C18) group.

6. The composition according to claim 5, in which the at least one anionic associative acrylic copolymer is chosen from terpolymers of methacrylic acid, ethyl acrylate, and polyoxyethylenated stearyl alcohol allyl ether containing 10 mol of ethylene oxide.

7. The composition according to claim 4, in which the at least one anionic associative acrylic copolymer is chosen from polymers formed from 20% to 60% by weight of (meth)acrylic acid, from 5% to 60% by weight of $C_1$-$C_4$ alkyl (meth)acrylate, from 2% to 50% by weight of monomer of formula (III), and from 0 to 1% by weight of a crosslinking agent which is a copolymerizable unsaturated polyethylenic monomer.

8. The composition according to claim 4, in which the at least one anionic associative acrylic copolymer is chosen from copolymers of (i) a monomer of formula (IV) below:

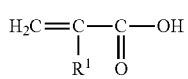

(IV)

in which $R^1$ denotes H or $CH_3$ or $C_2H_5$, and (ii) monomer of the following formula (V):

(V)

in which $R^1$ denotes H or $CH_3$ or $C_2H_5$, $R^3$ denotes a $C_{10}$-$C_{30}$.

9. The composition according to claim 4, in which the at least one anionic associative acrylic copolymer is chosen from polymers formed from a mixture of monomers comprising:

(i) acrylic acid, (ii) an ester of formula (V) as follows: $H_2C=CR^1-COOR^3$ (V)

in which $R^1$ denotes H or $CH_3$ and $R^3$ denotes an alkyl group containing from 12 to 22 carbon atoms, (iii) and optionally a crosslinking agent, which is a copolymerizable polyethylenic unsaturated monomer.

10. The composition according to claim 4, in which the at least one anionic associative acrylic copolymer is constituted of 95% to 60% by weight of acrylic acid, 4% to 40% by weight of $C_{10}$-$C_{30}$ alkyl acrylate and 0% to 6% by weight of a crosslinking polymerizable monomer,
or is constituted of 98% to 96% by weight of acrylic acid, 1% to 4% by weight of a $C_{10}$-$C_{30}$ alkyl acrylate and 0.1 to 0.6% by weight of a crosslinking polymerizable monomer.

11. The composition according to claim 4, in which the $\alpha,\beta$-monoethylenically unsaturated carboxylic acid (a) is chosen from acrylic acid, methacrylic acid or crotonic acid.

12. The composition n according to claim 4, in which the monomer (b) for the acrylic terpolymers (3) is chosen from methyl (meth)acrylate, ethyl (meth)acrylate or butyl (meth)acrylate.

13. The composition according to claim 4, in which the at least one anionic associative acrylic copolymer chosen from the acrylic terpolymers (3) is a terpolymer of methacrylic acid/methyl acrylate/condensate of dimethyl meta-isopropenyl benzyl isocyanate and polyoxyethylenated (40 OE) behenyl alcohol.

14. The composition according to claim 4, in which the at least one anionic associative acrylic copolymer is chosen from:
polymers of acrylic acid, methyl acrylate and 20 OE polyoxyethylenated stearyl methacrylate crosslinked with pentaerythrityl allyl ether or trimethylolpropane allyl ether; crosslinked polymers of acrylic acid, methyl acrylate and 25 OE polyoxyethylenated behenyl methacrylate;
polymers of acrylic acid, methyl acrylate and 25 OE polyoxyethylenated C12-C24 alkyl methacrylate;
polymers of methacrylic acid, ethyl methacrylate, polyethylene glycol C16-C22 alkyl ether methacrylate containing 25 ethylene glycol units and ether of 2-(6,6-dimethylbicyclo[3.1.1]hept-2-en-2-yl)ethyl methacrylate and polypropylene glycol containing 5 propylene glycol units/polyethylene glycol containing 25 ethylene glycol units;
polyoxyethylenated (20 OE) terpolymer of acrylic acid/ethyl acrylate/stearyl methacrylate; or polyoxyethylenated (25 OE) terpolymer of acrylic acid/ethyl acrylate/behenyl methacrylate.

15. The composition according to claim 1, in which the at least one hydrophilic gelling polymer is chosen from crosslinked copolymers of (meth)acrylic acid and of $C_1$-$C_4$ alkyl (meth)acrylate.

16. The composition according to claim 1, in which the anionic acrylic copolymers have a weight-average molecular weight of less than 500,000.

17. The composition according to claim 1, in which the content of the anionic acrylic copolymers is from 0.1% to 2% by weight, relative to the total weight of the composition.

18. The composition according to claim 1, in which, in the at least one lipophilic polymer, $R_1$ is constituted of alkyl radicals.

19. The composition according to claim 1, in which, in the at least one lipophilic polymer, at least 70% by weight of the $R_1$ groups are behenyl radicals.

20. The composition according to claim 1, in which, in the at least one lipophilic polymer, all the $R_1$ groups are behenyl radicals.

21. The composition according to claim 1, in which, in the at least one lipophilic polymer, the weight ratio of the sum of all the hydroxyethyl acrylate units to the sum of all the acrylate units bearing the $R_1$ group ranges from 1:15 to 1:1.

22. The composition according to claim 1, in which the at least one lipophilic polymer has a number-average molecular weight Mn ranging from 5000 to 9000 g/mol.

23. The composition according to claim 1, in which the at least one lipophilic polymer has a melting point ranging from 60° C. to 69° C.

24. The composition according to claim 1, in which the at least one lipophilic polymer is present in the composition in an amount ranging from 0.1% to 10% by weight, relative to the total weight of the composition.

25. A cosmetic process for caring for and/or removing makeup from and/or cleansing keratin materials which comprises applying the composition according to claim 1 to the keratin materials.

26. A cosmetic process for treating a keratin material, in which the composition of claim 1 is applied to the keratin material.

* * * * *